United States Patent [19]
Dellinger et al.

[11] Patent Number: 5,853,993
[45] Date of Patent: Dec. 29, 1998

[54] SIGNAL ENHANCEMENT METHOD AND KIT

[75] Inventors: Douglas J. Dellinger, Sunnyvale; SueAnn C. Dahm; Mark A. Troll, both of Palo Alto, all of Calif.

[73] Assignee: Hewlett-Packard Company, Palo Alto, Calif.

[21] Appl. No.: 735,381

[22] Filed: Oct. 21, 1996

[51] Int. Cl.$^6$ .............................. C12Q 1/68; C12N 15/00; C07H 21/02; C07H 21/04
[52] U.S. Cl. .......................... 435/6; 536/23.1; 536/24.3; 935/76; 935/77; 935/78
[58] Field of Search ..................... 435/6, 810; 935/76, 935/77, 78; 536/23.1, 24.3

[56] References Cited

U.S. PATENT DOCUMENTS

| | | | |
|---|---|---|---|
| 4,563,419 | 1/1986 | Ranki et al. | 435/6 |
| 4,751,177 | 6/1988 | Stabinsky | 435/6 |
| 4,882,269 | 11/1989 | Schneider et al. | 435/6 |
| 4,894,325 | 1/1990 | Englehardt et al. | 435/6 |
| 5,124,246 | 6/1992 | Urdea et al. | 435/6 |
| 5,437,977 | 8/1995 | Segev | 435/6 |
| 5,487,973 | 1/1996 | Nilsen et al. | 435/6 |
| 5,561,043 | 10/1996 | Cantor et al. | 435/6 |
| 5,627,030 | 5/1997 | Pandian et al. | 435/6 |
| 5,629,156 | 5/1997 | Shah et al. | 435/6 |
| 5,695,936 | 12/1997 | Mandrand et al. | 435/6 |

FOREIGN PATENT DOCUMENTS

| | | | |
|---|---|---|---|
| 124221 A1 | 11/1984 | European Pat. Off. | C12Q 1/68 |
| 2169403 | 7/1986 | United Kingdom | C12Q 1/68 |
| WO 93/07295 | 4/1993 | WIPO | C12Q 1/68 |

OTHER PUBLICATIONS

Vo, Thuong et al., "Targeting Pyrimidine Single Strands by Triplex Formation: Structural Optimization of Binding", *Nucleic Acids Research*, vol. 23, No. 15, 1995, pp. 2937–2944.

Matthews et al., Analytical Biochemistry 169: pp. 1–25 (1988).

Frazen et al., Lancet 10 Mar. 1984: pp. 525–527 (1984).

Chen et al., Molecular and Biochemical Parasitology 44: pp. 165–174 (1991).

Palva et al., Gene 15 :43–51 (1981).

*Primary Examiner*—W. Gary Jones
*Assistant Examiner*—Ethan Whisenant

[57] ABSTRACT

The invention discloses and claims a signal amplification method for detecting a target nucleic acid analyte having a homopolymeric region and a target sequence. The method comprises (a) contacting an analyte under hybridizing conditions with a multiplicity of reporter probes, each probe including a signal region and an oligonucleotide sequence which is complementary to, and capable of forming a stable hybrid with the analyte homopolymeric region, whereby the hybridization of multiple reporter probes to the homopolymeric region provides for signal amplification; and (b) forming an analyte:capture probe hybrid by contacting the analyte target sequence with a capture probe under hybridizing conditions.

16 Claims, 6 Drawing Sheets

SIGNAL ENHANCEMENT METHOD AND KIT

FIELD OF THE INVENTION

This invention relates to the detection of nucleic acids in a sample, in particular, to a signal enhancement method for increasing the detectability of a nucleic acid analyte in a sandwich hybridization assay.

BACKGROUND

For the past several decades, molecular hybridization has been an extremely useful tool for identifying and analyzing specific nucleic acid sequences in complex mixtures. The basic technique has undergone various changes that permit the simultaneous analysis of multiple sequences in a single assay (multiplexing) with increased speed and sensitivity of detection.

The sensitivity of detection must be sufficient to allow sequences present in the initial sample in single or low copy number to be reproducibly detected and distinguished from background noise. The signal-to-noise problem has been addressed in various ways, e.g., by amplifying the target nucleic acid sequences, by enhancing the signal generated by molecules associated with the hybridized sequences, and by reducing non-specific background binding.

Various sandwich hybridization techniques have been developed to detect specific sequences in nucleic acids. These include: a one-step sandwich hybridization assay in which two probes, one immobilized and one labeled, are bound to non-overlapping sequences in the target (U.S. Pat. No. 4,563,419); an amplification assay in which a primary probe contains non-overlapping sequences which are respectively complementary to the target DNA and to multiple signal-generating probes (U.S. Pat. No. 4,882,269); the formation of a triple helix between a single-stranded target sequence and two complementary oligonucleotide probes (U.S. Pat. No. 5,772,081); multihybrid formation using probes capable of binding to more than one nucleic acid target sequence (U.S. Pat. No. 4,894,325; U.S. Pat. No. 5,487,973); and the use of multimers capable of hybridizing directly or indirectly to a target nucleic acid sequence and to a second oligonucleotide sequence that is capable of binding multiple labeled oligonucleotides (U.S. Pat. No. 5,124,246).

The invention described herein is a method for achieving signal amplification that requires little manual handling, uses simplified signal enhancement reagents and is capable of being used with "microchip"-based genetic screening and diagnostic applications.

SUMMARY OF THE INVENTION

The invention disclosed and claimed herein provides a signal amplification method for detecting a target nucleic acid analyte having a homopolymeric region and a target sequence. The method comprises (a) contacting an analyte under hybridizing conditions with a multiplicity of reporter probes, each probe including a signal region and an oligonucleotide sequence which is complementary to, and capable of forming a stable hybrid with, the analyte homopolymeric region, and (b) forming an analyte: capture probe hybrid by contacting the analyte target sequence with a capture probe under hybridizing conditions.

In one embodiment of the invention, the capture probe is immobilized to a support prior to hybridization to the target analyte. In another, the capture probe is adapted for immobilization to the support surface, with immobilization taking place after the capture probe: target analyte: reporter probe complex is formed.

One objective of the invention is to provide a signal amplification method for detection of a target nucleic acid analyte having a naturally-occurring or synthetically-added homopolymeric region. The method is designed to minimize handling of the nucleic acid analyte, and to provide increased detection sensitivity without requiring amplification of the nucleic acid target itself.

A second objective is to provide a method of signal amplification that uses a universal reporter probe comprised of a signal region and an oligonucleotide sequence for multisite binding to a complementary homopolymeric region of any given nucleic acid analyte of interest.

A third objective of this invention is to provide a method of signal amplification wherein the analyte homopolymer sequence provides a region for multisite binding of reporter probes. Additional signal enhancement is realized through triple helix formation between reporter probes and the analyte homopolymeric sequence.

A fourth objective of this invention is to provide a method of signal amplification wherein the reporter probes are designed to contain stable stem-and-loop structures for attachment of multiple fluorophores using linkers of sufficient length and rigidity to minimize fluorescent quenching.

A final objective of this invention is to provide a kit for performing the signal amplification method of this invention, wherein the kit comprises a capture probe immobilized on a solid surface, reporter probes, and optional reagents for addition of homopolymeric regions to nucleic acid analytes and performing the hybridization reaction.

DETAILED DESCRIPTION OF THE INVENTION

Figure 1:
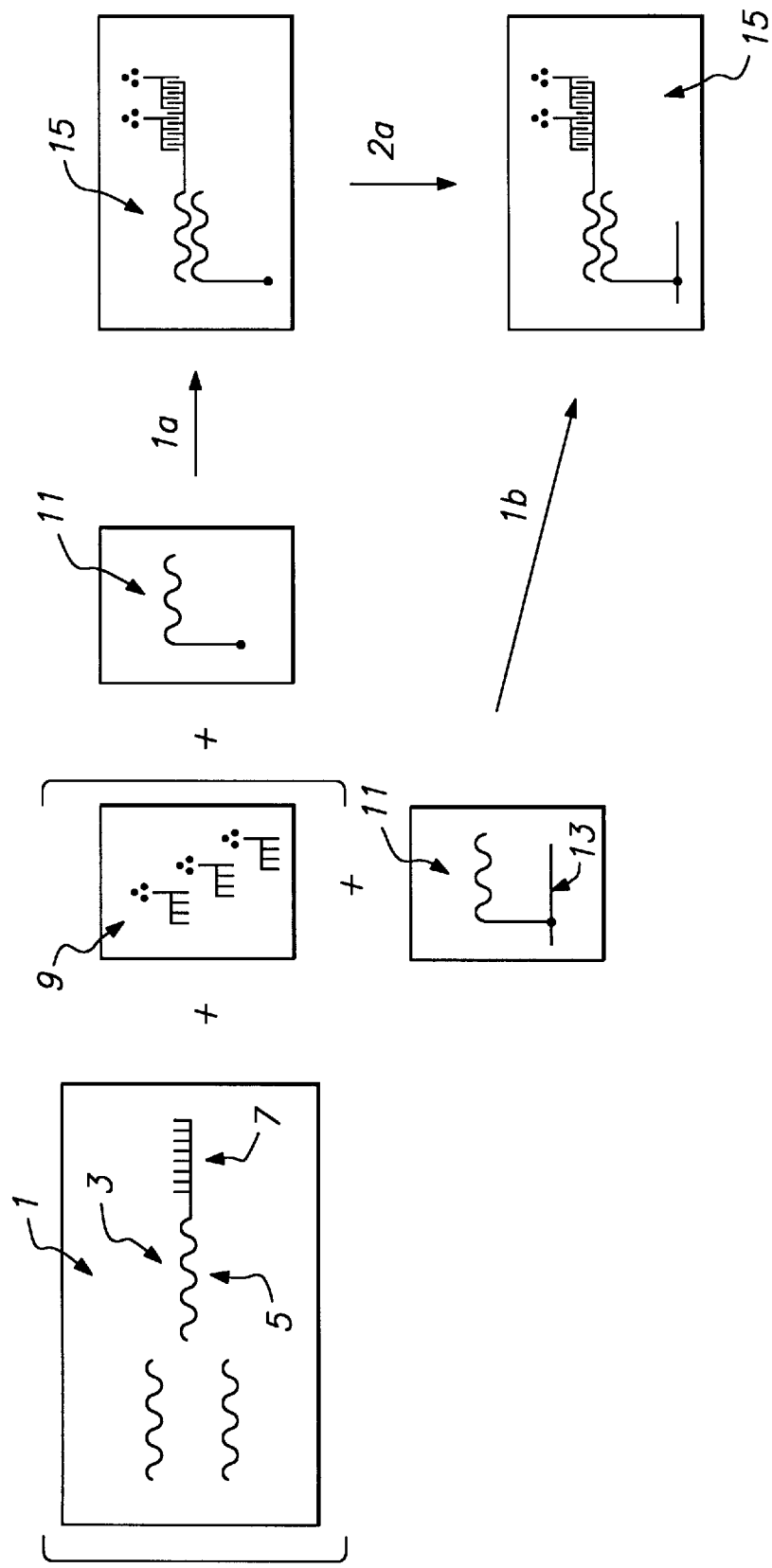
FIG. 1. A general schematic of the signal amplification assay.

Before the invention is described in detail, it is to be understood that this invention is not limited to the particular component parts or process steps of the methods described, as such parts and methods may vary. It is also to be understood that the terminology used herein is for purposes of describing particular embodiments only, and is not intended to be limiting. As used in the specification and the appended claims, the singular forms "a", "an", and "the" include plural referents unless the context clearly indicates otherwise.

Definitions

In this specification and in the claims which follow, reference will be made to a number of terms which shall be defined to have the following meanings:

The term "homopolymeric region" refers to a nucleotide sequence containing a tract of purine or pyrimidine bases.

The term "homopolymeric tailing" refers to the addition of a homopolymeric region to the 3' or 5' terminus of a nucleic acid by enzymatic or chemical methods. This addition can be made by stepwise addition of nucleotides or by ligation of a preformed homopolymer.

The term "oligonucleotide" refers to a short sequence of nucleoside monomers (usually 6 to 100 nucleosides) joined by phosphorus linkages (e.g., phosphodiester, alkyl and aryl-phosphonate, phosphorothioate, phosphotriester), or non-phosphorus linkages (e.g., peptide, sulfamate, and others). An oligonucleotide may contain modified nucleosides having modified bases (e.g., 5-methyl cytosine) and modified sugar groups (e.g., 2'O-methyl ribosyl, 2'O-methoxyethyl ribosyl, 2'-fluoro ribosyl, 2'-amino ribosyl, and the like). Oligonucleotides comprise naturally-occurring or synthetic molecules of double- and single-stranded DNA and double- and single-stranded RNA with circular, branched or linear shapes and optionally including domains capable of forming stable secondary structures (e.g., stem-and- loop and loop-stem-loop structures ).

The term "target nucleic acid analyte" refers to a nucleic acid whose presence or absence in a sample is desired to be detected. The analyte is characterized by the presence of a homopolymeric region at the 3' or 5' end of the molecule (e.g., mRNA-poly A; HCV RNA-poly U).

The term "target sequence" refers to a unique nucleotide sequence in a target nucleic acid analyte which is recognized by a capture probe.

The term "probe" refers to a single-stranded oligonucleotide sequence that will recognize and form a hydrogen-bonded duplex with a complementary sequence on a nucleic acid analyte.

The term "reporter probe" refers to a probe that includes a "signal region" and an oligonucleotide sequence that specifically binds to the homopolymeric region of the nucleic acid analyte and nowhere else. This homopolymeric-binding sequence is referred to herein as the oligonucleotide target binding region.

The term "signal region" refers to a polymer (e.g., an oligonucleotide, protein or polysaccharide) that is labeled with, or naturally contains, one or more chemical groups having a physical or chemical characteristic capable of measurement or detection by an appropriate detection system.

The term "capture probe" refers to a probe that possesses a sequence complementary to a predetermined region on the target analyte other than the homopolymeric region and is capable of forming a stable hybrid with the target analyte under selected stringency conditions. The capture probe is immobilized on a solid support for detection of the reporter probe: target nucleic acid analyte complex.

The term "hybrid" refers to a double-stranded nucleic acid molecule formed by hydrogen bonding between complementary nucleotides.

The term "poly A" refers to polyadenylic acid.

The term "$(dT)_n$" refers to deoxyoligothymidylate n nucleotides long.

The term "$(U)_n$" refers to oligouridylate n nucleotides long,

The term "$(U')_n$" refers to an oligouridylate analog, n nucleotides long, e.g., oligo-(2'-deoxy-2'-methyl)- uridylate, oligo-(2'-deoxy-2'-methoxyethyl)-uridylate, oligo-(2'-deoxy-2'-fluoro)-uridylate, oligo- (2' deoxy-2'-amino)-uridylate or other modifications of uridylate that strengthen base pairing in duplex and triplex structures containing such modified uridylate groups.

The term "triple helix" refers to a structure formed by the base pairing of a single-stranded nucleic acid (or oligonucleotide) to a double stranded nucleic acid (or oligonucleotide).

The term "hairpin" refers to an oligonucleotide structure having a single stranded loop attached to a double stranded stem.

The term "loop-stem-loop" refers to a "hairpin" enclosed by a loop. This structure can be formed from a circular oligonucleotide having two complementary binding domains joined by linkers that are not complementary to each other or to the complementary binding domains. (See, e.g., Vo et al, *Nucleic Acids Res.* 23: 2937–2944 (1995).

The term "stringency" refers to hybridization conditions that affect the stability of hybrids, e.g., temperature, salt concentration, pH, formamide concentration, and the like. These conditions are empirically optimized to maximize specific binding, and minimize nonspecific binding, of probe to target.

The term "signal enhancement" or "signal amplification" refers to the signal intensity produced by multiple reporter probes hybridized to a target nucleic acid analyte relative to the signal intensity produced by a single reporter probe hybridized to the target nucleic acid analyte.

The term "fluorophore" refers to a chemical group having fluorescence properties.

The term "alkyl" refers to a straight chain divalent hydrocarbon radical containing no unsaturation.

The term "alkene" refers to a straight chain divalent hydrocarbon radical containing one or more double bonds.

The term "alkyne" refers to a straight chain divalent hydrocarbon radical containing one or more triple bonds.

The term "aryl" refers to a divalent unsaturated aromatic carbocyclic radical having one or more rings.

The term "optionally" means that the subsequently described event or circumstance may or may not occur and that the description includes instances where said event or circumstance occurs and instances in which it does not.

The present invention provides a method for enhancement of detection of nucleic acid hybridization by attachment of multiple reporter probes to a homopolymeric region at the 3' or 5' terminus of a nucleic acid analyte (FIG. 1).

Referring to FIG. 1, a biological sample (1) containing a target nucleic acid analyte (3) having a target sequence (5) and a homopolymeric region (7) is reacted under hybridizing conditions with multiple reporter probe molecules (9) and a capture probe (11) to form a reporter probe: target analyte: capture probe hybrid (shown generally at (15)). The capture probe is immobilized to a solid support (13) and functions to separate the target analyte from other molecules in the mixture.

The hybridization of capture probe and reporter probes to target analyte can be carried out in solution, followed by immobilization of the capture probe to a support (FIG. 1, steps 1a and 2a) (Syvanen et al (1986), *Nucleic Acids Res.* 14: 5037–5048). The capture probe is adapted for binding to the support (e.g., by linking the probe to a molecule such as biotin having high affinity for complementary binding partner such as streptavidin on the support surface, or by attaching the probe to a magnetic bead for binding to a magnetized support). Solution hybridization occurs at a more rapid rate than would otherwise occur with hybridization to an immobilized probe.

Alternatively, the capture probe can be immobilized on a solid support prior to hybridization with target analyte or target analyte: reporter complexes (FIG. 1, step 1b). This procedure has the advantage of ease of handling and a lower level of background noise. Various types of solid supports and attachment methods can be used to immobilize oligonucleotides (See, e.g., U.S. Pat. No. 5,478,893; Mandenius et al, *Anal Biochem.* 157: 283 (1986); and U.S. Pat. No. 5,474,796).

This method of this invention has particular advantages over other methods when it is used to detect RNA species with naturally-occurring homopolymeric tails (e.g., most eucaryotic mRNAs, some viral RNAs). RNA preparation and handling are kept to a minimum to avoid nonspecific RNA degradation; the hybridization of RNA to reporter molecules can be carried out in solution thereby allowing a more rapid rate than would otherwise be possible with immobilized target; and the concentration of the capture probe can be adjusted to permit hybridization under target-limiting conditions thereby conserving sample. However, any RNA or DNA target can be prepared for use in this assay by employing homopolymer tailing methods such as those described in Deng & Wu (1983) *Methods in Enzymology*, vol 100, 96–116 (terminal transferase); Edmonds, (1982) *The Enzymes*, vol. XV, 217–244 (poly (A)-adding enzymes; Schaefer, *Anal. Biochem.*227: 255–273 (1995) (ligation, PCR amplification and cloning); Kanaya & Yanagawa, *Biochemistry* 25: 7423–7430 (chemical ligation).

The reporter probes for use in this invention include a signal-generating region comprising one or more molecules capable of producing a detectable signal and an oligonucleotide sequence that specifically binds to the homopolymeric region of the nucleic acid analyte and nowhere else. The particular advantage of this probe design is its simplicity: the specificity of the probe for any nucleic acid analyte is determined solely by the analyte homopolymeric region. These probes are easily synthesized and can be used universally with a large number of different analyte species.

Factors Affecting Signal Enhancement

The signal enhancement capability of this invention depends upon: (1) the number of moles of reporter probe bound per mole of captured nucleic acid target analyte; and (2) the reporter probe labeling density (i.e., the number of signal-producing molecules/probe).

A. Increased ratio of reporter probes/target analyte

Figure 2A:
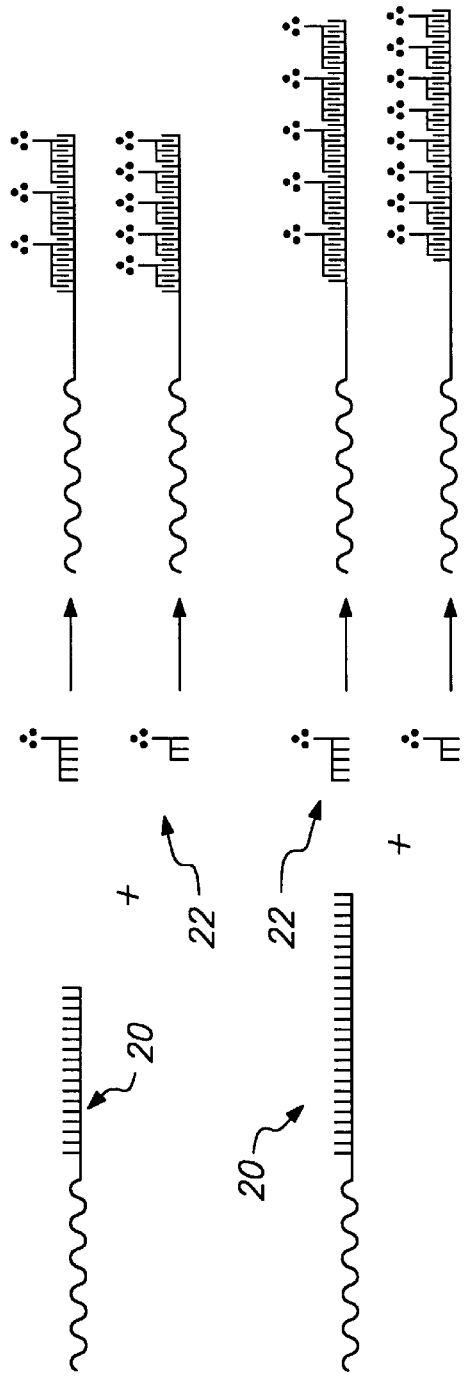
FIGS. 2A and 2B. Increasing the number of reporter probes bound to to a target analyte by varying the length of the homopolymeric binding region (A) and by forming a triple helix (B).
Figure 2B:
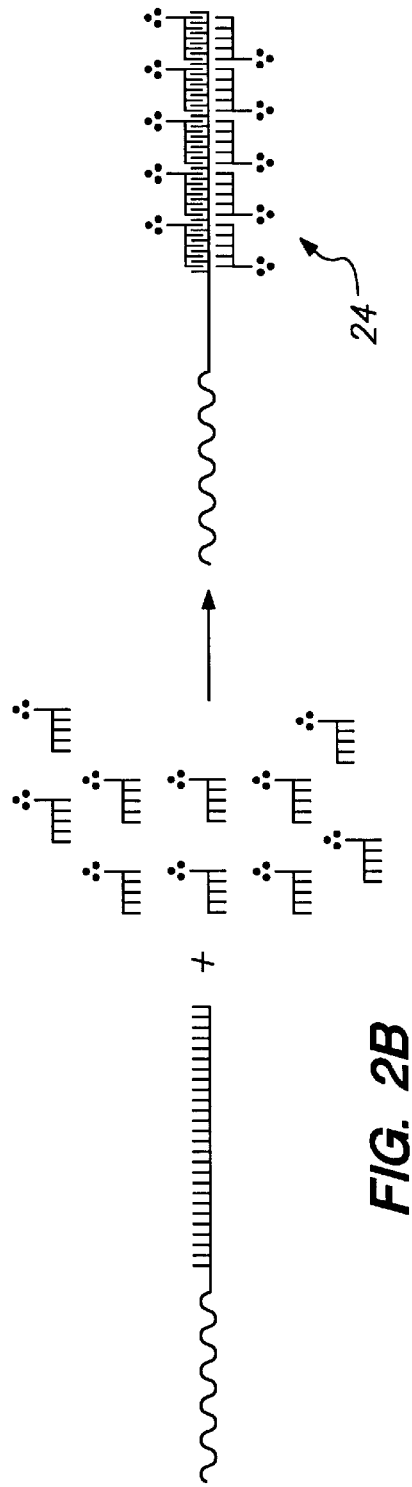

The molar ratio of reporter probes/target analyte can be increased in two non-mutually exclusive ways: by varying the respective lengths of the analyte homopolymer region (FIG. 2A, (20)) and the complementary reporter probe oligonucleotide sequence (FIG. 2A, (22)), and by carrying out hybridization reactions under conditions suitable for triple helix formation between probes and target analyte (FIG. 2B, (24)).

1. Homopolymer length

Well-known methods can be used to synthesize reporter probes with homopolymeric sequences of any desired length. The exact length of a probe is optimized to provide for stable hybrid formation at a reasonably rapid rate (e.g., from less than one to several hours) and a sufficient density of reporter probes bound to the target analyte to satisfy the detectability requirements of the assay. Preferably, the reporter probe oligonucleotide will be from about 8 to about 30 base pairs long. The procedure for optimization of probe length is within the capability of an ordinary skilled worker in this field.

The length of naturally-occurring homopolymeric tails on nucleic acid analytes can be shortened or lengthened by enzymatic and/or cloning methods. For example, the length of poly-A sequences on mature populations of mRNA (circa 50–200 nucleotides long) can be shortened to 10–25 nucleotides by the use of specific poly A nuclease enzymes (Jacobson and Peltz, *Annu. Rev. Biochem.* (1996), 65: 693–739 at 699, and references cited therein). If it is desired to achieve a uniform distribution of poly A lengths, e.g., for the purpose of quantitating a specific mRNA transcript, cloning methods are available (see, e.g., RLM-RACE protocol reviewed in B.C.Schaefer, *Anal.Biochem.* 227, 255–273 (1995). Alternatively, the naturally occurring poly A tails can be removed and replaced with a tail of a predetermined length (see, e.g., *Proc.Natl.Acad.Sci. U.S.A.* 90, 3806 (1993). The length of a poly A tail on a specific mRNA can be measured by PCR amplification using an oligo(dT) anchor primer and message-specific primer as described by Sallés and Strickland, *PCR Methods and Applications* (1995), pp. 317–321.

Homopolymeric tails can also be added to nucleic acid analytes that normally lack these sequences, as discussed above. If desired, tailing can be performed after capturing the analyte with an immobilized capture probe.

Figure 3:
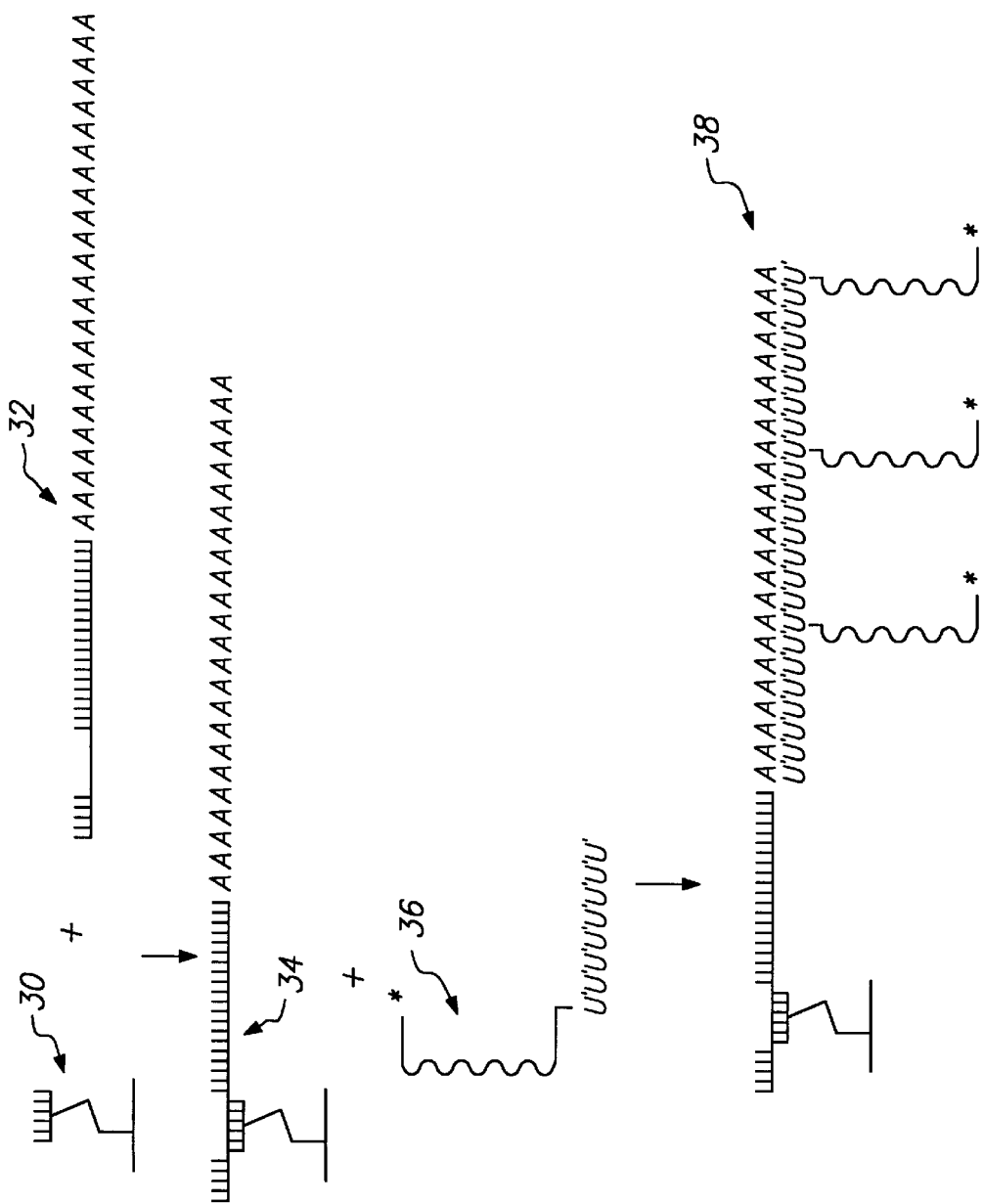
FIG. 3. A double helix signal amplification assay using a poly A-RNA target analyte (SEQ ID no1).

An embodiment of the assay adapted for detection of poly A-RNA analyte is illustrated in FIG. 3. Referring to FIG. 3, an immobilized capture probe (30) is contacted under hybridizing conditions with a polyadenylated RNA analyte (32) to form a capture probe: analyte hybrid (34). The unreacted RNA is removed by washing. A second hybridization between the capture probe: poly A-RNA analyte hybrid and an oligo-U' reporter probe (36) results in the formation of a hybrid between poly A and oligo-U' (38). After removal of the nonhybridized probes by washing, the reporter group signal is detected.

The use of an oligo-U' with a 2'-ribosyl modification (e.g., 2'-O-methyl, 2'-O-methoxyethyl, 2'-fluoro, and 2'-amino) increases the binding constant and protects the probe from RNAse digestion. In general, these modified nucleosides can can be made inexpensively and in high yield by procedures known to one skilled in the art, as shown in FIG. 4.

Figure 4A:
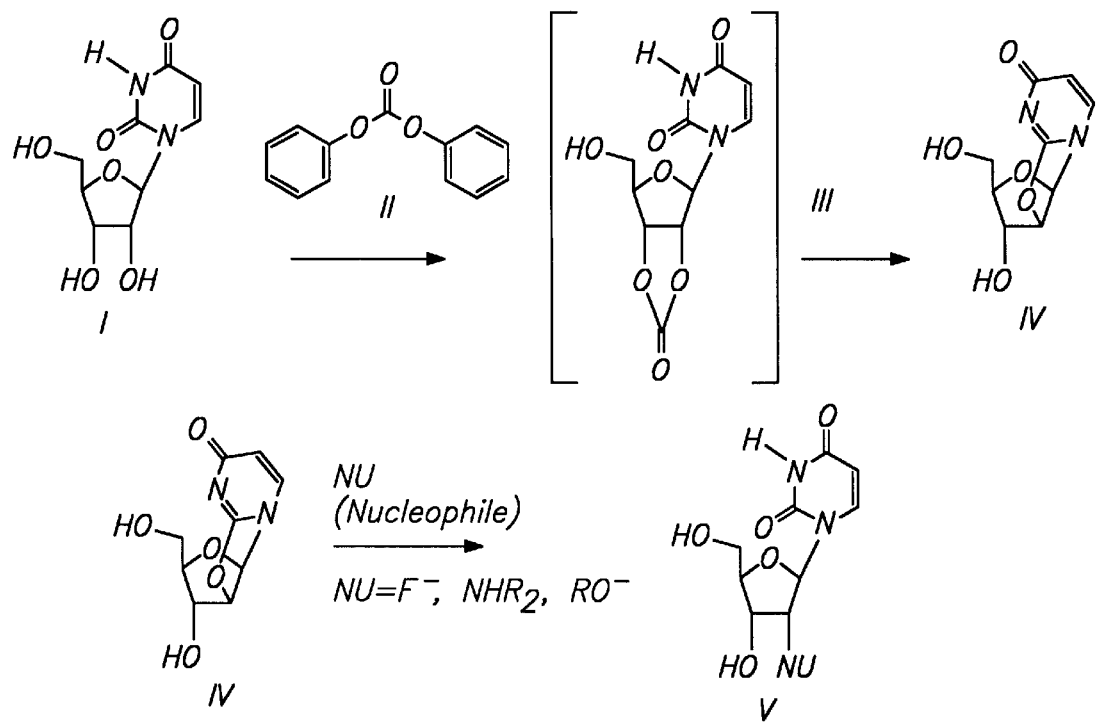
FIG. 4. Synthesis of modified nucleosides.

As shown in FIG. 4A, uridine (I) and diphenylcarbonate (II) are heated in the presence of sodium carbonate in dimethylformamide to form a 2'3'-cyclic carbonate (Ill) which results in the formation of the 2,2'anhydro-1β-D-arabinofuranosyluracil (IV). The reaction of a compound of formula IV with a nucleophile will produce a 2'-modified nucleoside.

Figure 4B:
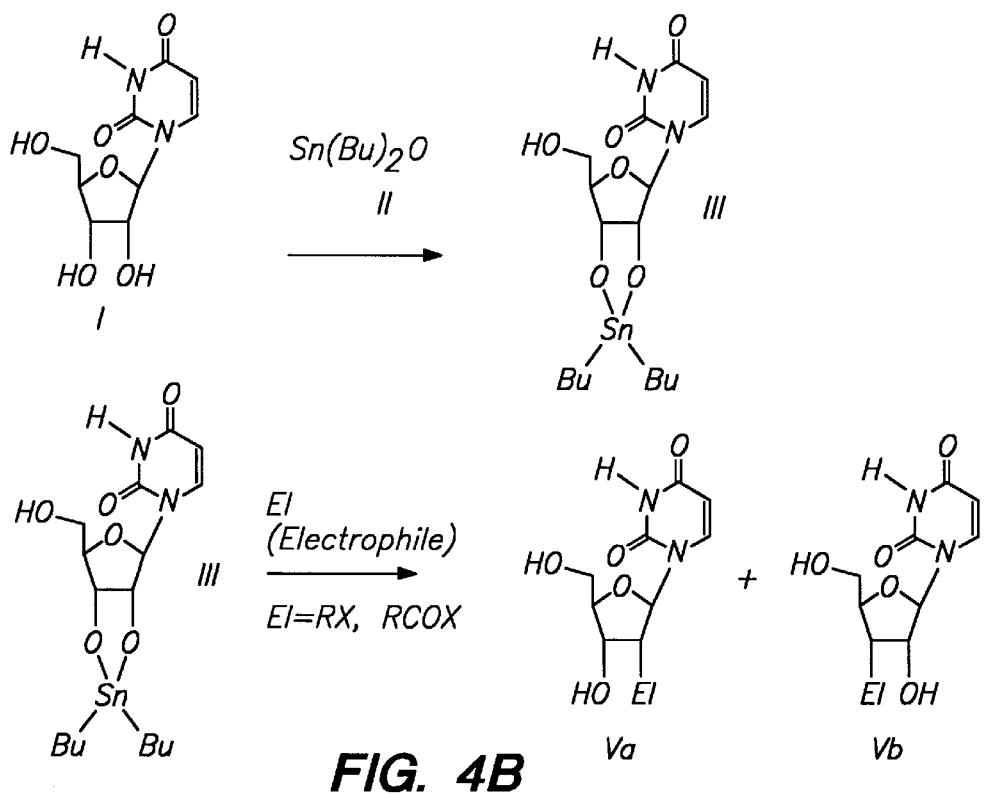

Alternatively, as shown in FIG. 4B, uridine (I) is reacted with dibutyltin oxide (II) dissolved in methanol to produce 2',3'-(dibutylstannylene)uridine (III). The reaction of a compound of formula III with an electrophile, e.g., methyl iodide or acetyl chloride, will produce a mixture of 2' and 3' modified nucleosides (Va, Vb), which can be separated chromatographically.

2. Triple helix formation

Short stretches of bases in single-stranded DNA or RNA can form triplexes with double-stranded DNA, RNA or DNA/RNA. A linear single-stranded homopyrimidine or homopurine oligonucleotide can bind in the major groove of a Watson-Crick paired double helix by forming Hoogsteen hydrogen bonds with a purine tract of the duplex. See, generally, Chapter 2 in *Laboratory Techniques in Biochemistry and Molecular Biology*, vol.24, ed., PC van der Vliet, Elsevier (1993). A circular oligonucleotide containing two pyrimidine-rich or purine-rich domains can form a stable triplex with a single-stranded purine or pyrimidine target, respectively (see Vo et al, *Nucleic Acids Res.* 23: 2937–2944 (1995) and references cited therein). Triple helix formation has been used for DNA isolation (Ito, *Proc. Natl. Acad. Sci. U.S.A.* 89, 495 (1992) and in the design of antisense and ribozyme agents (Holland & Hoffman, *Nucleic Acids Research* 24: 2841–2848 (1996)).

Figure 5:
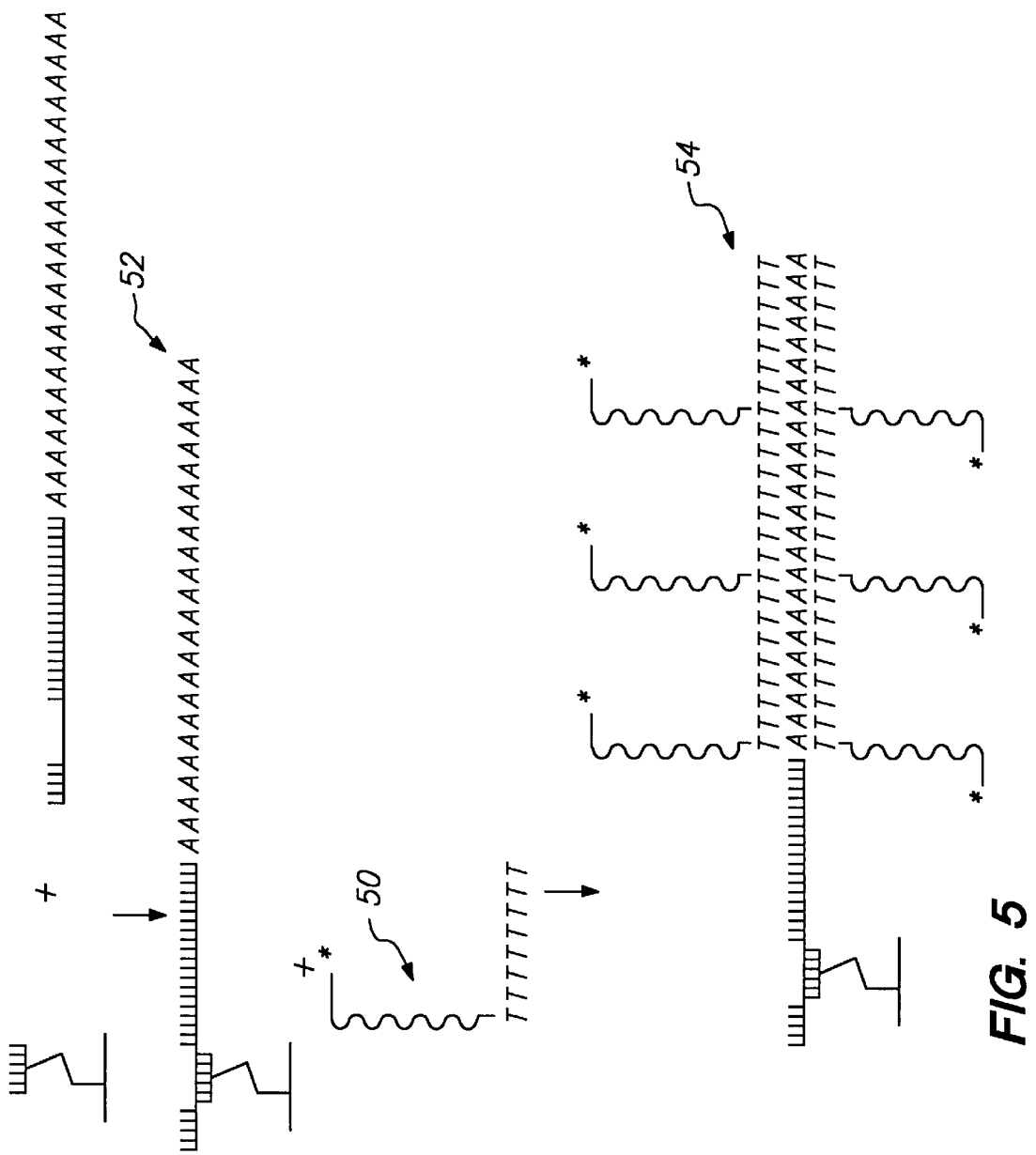
FIG. 5. A triple helix signal amplification assay using a poly A-RNA target analyte (SEQ ID no1).

In the present invention, triple helix formation is used as a means for enhancing the detection of a nucleic acid analyte. This is illustrated in FIG. 5. In FIG. 5, multiple reporter probes having oligo-dT sequences (50) are bound to the same poly-A sequence of the captured target analyte (52) to form a triple helix structure (54). The thermal stability of each $(T-A-T)_{15}$ triplex is approximately 30° C. greater than that of a poly A-dT duplex of comparable length (as determined from the melting temperature ($T_m$) in 100mM NaCl) (Shea et al, (1990) *Nucl. Acids Res.*18: 4859–4866). Modifications of the reporter probe that result in increased base-stacking interactions, van der Waals interactions, and hydrogen bonding between the incoming strand and the duplex will stabilize the triplex. The use of nucleoside analogs to increase the formation and stability of triple helixes is described in Ts'o et al, PCT publication, WO 93/07295.

The rate of formation of a triple helix is slower than for double helix formation. It is known that triple helix formation is inhibited at sodium ion concentrations that promote the rate of reassociation of single strands to form duplexes. This inhibitory effect can be reversed by magnesium ions (Maher et al (1990) *Biochemistry* 29: 8820–8826). Spermine tetrahydrochloride stimulates the rate of triple helix formation (Moser & Dervan (1987) *Science* 238: 645). Those of ordinary skill in this technology will appreciate and know how to vary the hybridization conditions to promote the formation and stability of triple helices.

B. Reporter Probe Labeling Density

The reporter probes preferred for use in this invention have a signal region comprising a polymer, e.g., an oligonucleotide, a protein or a polysaccharide, that is labeled with multiple signal-emitting groups. The signal region is adapted for covalent attachment to either or both the 3' and 5' terminus of the oligonucleotide target binding region or an internal position. Where necessary, the attachment points can be functionalized using well-known chemical reactions (see,e.g.,U.S. Pat. No. 5,521,298). The signal-emitting group can be any moiety that is capable of producing a detectable signal by itself or combined with other moieties. Useful types of signals include electromagnetic radiation (e.g., fluorescence, chemiluminescence), electrical, ionic, chemical and mechanical signals or any combination of these.

Detection Sensitivity

A. Signal intensity

The detection sensitivity of a signal will depend on the instrumentation used for detection, the intensity of the signal and the signal-to-noise ratio. It is often useful to label biological molecules with fluorescent groups to aid in detecting their presence. Fluorescent signals are one type of signal preferred for use in this invention. Aside from instrument-determined factors, the fluorescence intensity of a particular dye will depend on the quantum yield and maximum molar extinction coefficient. These molecular properties are strongly influenced by the specific environmental conditions of the assay (e.g., solvent polarity, pH, presence of diffusable molecular quenchers) and by the local concentration of fluorescent groups on the biological molecule. See generally, Joseph R.Lakowicz, *Principles of Fluorescence Spectroscopy*, Plenum Press (1986).

A commonly encountered difficulty in achieving a high labeling density of fluorescent probes on a biological molecule is fluorescence quenching. Quenching refers to any process by which the fluorescence intensity of a given species is reduced. Fluorescence quenching due to complex formation (static quenching) occurs when the quenching species is bound to the fluorescent one, for example, by hydrophobic, charge-transfer and/or Van der Waals forces. In addition, quenching can be produced by the transfer of excited state energy from donor to acceptor molecule without the appearance of a photon (energy transfer). The effective energy transfer distance is a function of the lifetime of the excited state, the angular orientation of the donor and acceptor molecules, the refractive index of the solvent and the spectral overlap between donor and acceptor. The rate of energy transfer varies with the inverse sixth power of the distance between donor and acceptor out to about 5 nm, and beyond that, with the inverse seventh power. The distance at which half the excited state energy is transferred (i.e., fluorescence is reduced by 50%) is typically 2 to 5 nm (i.e., 20 to 50 Å), which is in the same range as the diameter of many proteins and the diameter of a nucleic acid double helix.

Fluorescent labeling of biological molecules must be carried out in a way that avoids self-quenching and energy-transfer quenching. Fluorescent self-quenching is produced by the stacking of planar hydrophobic regions of fluorophores at high local concentrations. These stacking interactions perturb the molecular orbital structures of the affected molecules and reduce their capacity for fluorescence emission. Thus, with increased fluorophore concentration, the incremental enhancement of fluorescence will decrease.

There are several strategies for dealing with the problem of complex formation which, to some extent will reduce other quenching effects as well. These include: (1) making chemical modifications to the fluorescent species that do not affect their fluorescent properties but make it difficult for molecules to aggregate and (2) attaching the fluorescent species to a polymeric structure which holds them apart.

The ability to keep fluorophores that are attached to a common polymer from contacting each other depends on the distance between the attachment points and the flexibility of the linkages. A double or triple helix structure such as a nucleic acid (or an agar polysaccharide) provides a rigid framework with defined attachment points or regions. Nucleic acid duplexes and molecules of similar structure have persistence lengths of about 50 Å or more. (The persistence length is a measure of the statistical tendency of a polymer chain to remain in a straight line rather than coiled). To minimize other transfer mechanisms, the attached fluorophores should be spaced apart, preferably by 30 Å, more preferably by 50 Å, most preferably by 100 Å. For the closest fluorophores, the preferred angular orientation is near-orthogonal. For example, the bases in a DNA oligonucleotide can be labeled every fifth base. When bound to another complementary nucleic acid, the double-helix structure would then put adjacent labels on opposite sides of the helix, which is about 20 Å in diameter. With stiff linkers attaching the tag moieties to the polymer, the tags could easily be kept at least 30 Å apart. In many cases, this would suffice to reduce quenching to negligible levels. It should be clear that other spacing intervals, such as every third base, might be equally effective.

The dye linkers contemplated for use in this invention are selected from alkyl, alkene and alkyne, aryl and polyethylene glycol groups. Unsaturated hydrocarbons are preferred, and polyethylene glycols are most preferred. These linkers will have lengths of about 2 to about 200 carbons.

In the practice of this invention, oligonucleotides, proteins or polysaccharides are preferred polymers for reporter probe signal regions. However any artificial polymer having the requisite properties of a signal region would be suitable. Particularly preferred are polymers having one or more stable secondary structures capable of providing a scaffold for linkage of multiple signal groups. A hairpin comprised of a double-stranded stem and a single-stranded loop region is one type of preferred signal region. Optionally, the hairpin is linked to the target-recognition sequence of the reporter probe by a $(dT)_n$ linker, where n is an integer from 8 to 30.

Figure 6:
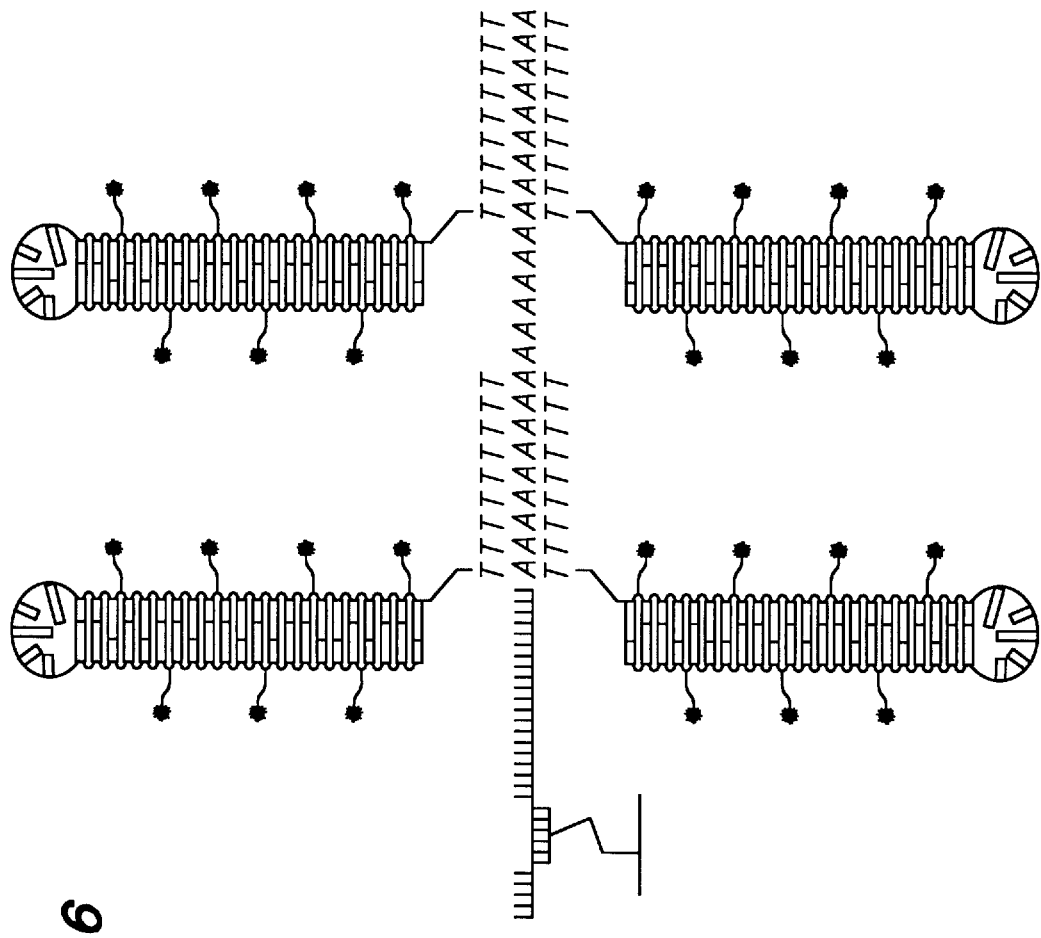
FIG. 6. Illustration of multi-labeled hairpin reporter probes for SEQ ID no1 signal amplification.

Hairpin structures can be synthesized chemically (e.g., by phosphoramidite chemistry), enzymatically (e.g., using T7 RNA polymerase and synthetic DNA templates), and by recombinant methods (see, e.g., U.S. Pat. No. 5,208,149). The size, sequence, and structural variations that give rise to stable hairpin oligonucleotide-containing structures, and their methods of synthesis are described in Heus & Pardi, Science 253: 191 (1991); Williamson & Boxer, Biochemistry 28: 2819–2831 (1989); Turner et al, Annu. Rev. Biophys & Biophys Chem. 17: 167 (1988) and Vo et al, Nucleic Acids Res. 23: 2937–2944 (1995). The hairpin structures of use in this invention will have a length sufficient to ensure complementary base pair formation under the selected hybridization conditions and to serve as a scaffold for the attachment of multiple dyes spaced appropriately to avoid quenching, as discussed above. FIG. 6 illustrates the use of a hairpin-type reporter probe in the triple helix assay of this invention.

In the practice of this invention, proteins are also useful for signal enhancement. Stable fluorescent proteins found in nature such as the phycobilirubins are particularly preferred. In R-phycoerythrin, for example, the number of fluorophores/mole of protein is greater than 30, and the molar extinction coefficient is 20 × greater than for fluorescein.

B. Signal-to-noise ratio

The detection sensitivity of the assay is increased not only by signal enhancement but also by reduction of background noise. This background noise could arise from non-specific binding between reporter probes, nucleic acids and surfaces within the hybridization chamber. Hybridization and wash procedures are chosen to minimize nonspecific hybridization and to remove unbound material. This subject is reviewed in Wahl et al, Molecular hybridization of immobilized nucleic acids: theoretical concepts and practical considerations, In Methods in Enzymology, Vol. 152, Chapter 43, pp. 399–407 (1987), Academic Press; G.H. Keller & M.M. Manak, Section 1 and 6, In: DNA Probes, 2nd Ed. Stockton Press). Those skilled in the art will know how to optimize hybridization parameters to achieve high signal-to-noise ratios.

The present invention uses capture hybridization and washing to effect the separation of unbound from hybridized material. A capture probe is used to detect and isolate the target analyte from other nucleic acid molecules in the sample. The target analyte is hybridized to the capture probe, which typically contains at least eight contiguous nucleotides that are homologous to a portion of the target nucleic acid in the sample. The nucleotide sequence of the target recognition moiety of the capture probe may vary in length from about 8 to about 50 nucleotides, but is preferably about 12 to 25 nucleotides. A sequence of these lengths is easily synthesized and is unlikely to give rise to secondary structures. One skilled in the art will know how to select a capture probe sequence length appropriate to bind the analyte target sequence with specificity and stability.

It should be understood that the above description is intended to illustrate and not limit the scope of the invention. Other aspects, advantages and modifications within the scope of the invention will be apparent to those skilled in the art to which the invention pertains.

The following example is put forth so as to provide those of ordinary skill in the art with a complete disclosure and description of how to use the method of the invention, and is not intended to limit the scope of what the inventors regard as their invention.

EXAMPLE

Example 1

Signal Enhancement Hybridization Assay

A. Synthesis of Target Analyte and Probes

The target analyte was a T7 RNA transcript having the following sequence:

GGGACACTCCACCATAGATCACTCCCCT-GTTTTTCGCAGAAAGCGTCTA GCCATG$(A)_{50}$ (SEQ ID no2).

The capture probe (5' ACAGGGGAGTGATCTATGGTG-GAGT 3') (SEQ ID no3) and fluorescein-labeled reporter probes (5' CATGGCTAGACGCTTTCTGCG 3') (SEQ ID no4) (control reporter sequence), oligo-2'-$(FU)_{15}$, and oligo-2'-$(FU)_{25}$) were synthesized on an ABI Model 394 DNA synthesizer. The 3' termini of the reporter probes were labeled with fluorescein phosphoramidite. Fluorescein phosphoramidite and dT amidite were purchased from Glen Research. 2'-deoxy-2' fluoro uridine (2'-FU) phosphoramidite was purchased from RI Chemical.

Hairpin reporter probes having the control reporter sequence shown below or oligo-2'-(FU) attached to the 3' end of the (dT) linker (not shown) can also be used to detect the above target analyte. Asterisks denote fluoresceinated positions.

```
        A A
       G   A
      *C—G
       T—A
       G—C
      *C—G
       A—T
       A—T
      *C—G
       T—A
       G—C
      *C—G
       T—A
       T—A
      *C—G
       A—T
       A—T
      *C—G
       A—T
       G—C
      *C—G
       G—C
       A—T
      *C—G
       T—A
       T—A
5'*C—GTTTTCATGGCTAGACGCTTTCTGCG 3' (SEQ ID NO 5)
```

B. Hybridization Assay

Target analyte (1 μM) was mixed with oligo FU-3' fluorescein (10 μM), or control reporter probes in 6× SSP buffer(1.1M NaCl, 60 mM $Na_2PO4$, pH 8) containing 5 mM $MgCl_2$ and 1 mM spermine at 4° C. for 1 to 3 hours. The incubation was continued for 3 hours at 4° C. in the presence of a capture probe immobilized on a glass slide. The hybridization chamber (100 μl) was washed three times with 1 ml of 0.1× SSP (18 mM NaCl, 1mM $Na_2PO4$, pH 8) containing 0.08 mM $MgCl_2$ and 0.02mM spermine.

Fluorescence was detected and quantified using a Molecular Dynamics Fluorimager instrument. Using the oligoribonucleotide target analyte of Example 1A, the signal intensities of the fluoresceinated reporter probes listed below when normalized to the signal intensity of the control reporter probe (=1) were: oligo-2' $(FU)_{15}$: 6; and oligo-2' $(FU)_{25}$: 4.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

---

What is claimed is:

1. A signal amplification method for detecting a target nucleic acid analyte having a homopolymeric region and a target sequence, wherein said homopolymeric region is poly A at the 3' terminus of said target nucleic acid analyte comprising the steps of:
   (a) contacting said analyte under hybridizing conditions with a multiplicity of reporter probes to form a triple helix, said probes comprising:
      (i) a signal region; and
      (ii) an oligonucleotide sequence, wherein said oligonucleotide sequence is complementary to said analyte homopolymeric region for forming a stable hybrid therewith, and
   wherein said reporter probes hybridize with said analyte homopolymeric region to form a triple helix and wherein the hybridization of multiple reporter probes to said analyte homopolymeric region provides for amplification of the detection signal and;
   (b) forming an analyte:capture probe hybrid by contacting said analyte target sequence with a capture probe under hybridizing conditions.

2. The method of claim 1, wherein step (a) is performed in solution and step (b) is carried out with an immobilized capture probe.

3. The method of claim 1, wherein steps (a) and (b) are performed in solution, and said analyte:capture probe hybrid formed in step (b) is subsequently bound to a surface for detection thereupon.

4. A signal amplification method for detecting a target nucleic acid analyte having a 3' terminus having a polyA region and a target sequence, comprising the steps of:

(a) contacting said analyte under hybridizing conditions with a multiplicity of reporter probes, said probes comprising a fluorescent polymer comprising an oligonucleotide linked to a fluorophore, wherein said oligonucleotide is a linear polymer comprising (dT)n, or (U)n, where n is an integer between 8 and 30; and wherein the hybridization of multiple reporter probes to said analyte polyA region provides for amplification of the detection signal; and
   (b) forming an analyte:capture probe hybrid by contacting said analyte target sequence with a capture probe under hybridizing conditions.

5. The method of claim 4, wherein said fluorophore is linked to said polymer by a phosphoramidite linker.

6. The method of claim 4, wherein said linker has length and rigidity characteristics sufficient to minimize the occurrence of fluorescence quenching of fluorophores of said fluorescent polymer when said reporter probes are hybridized to said analyte poly A region.

7. The method of claim 6, wherein said linker is selected from the group consisting of alkyl, alkene, alkyne, aryl and polyethylene glycol chains.

8. The method of claim 7, wherein said linker is an alkene or alkyne group from about 2 to about 200 carbons in length.

9. The method of claim 7, wherein said linker is a polyethylene glycol of the formula $H(OCH_2CH_2)_nOH$, where n is an integer from 4 to about 200.

10. The method of claim 4, wherein:
    (a) said oligonucleotide comprises a stable hairpin structure linked to multiple fluorophores; and
    (b) said hairpin structure is covalently linked at its 5' or 3' terminus.

11. The method of claim 4, wherein:

said oligonucleotide comprises a circular molecule having self-complementary homopolymeric domains, and said circular molecule is linked to multiple fluorophores; wherein:

under hybridizing conditions said domains interact with one another to form a stable hybrid thereby to convert said circular molecule into a loop-stem-loop structure and said poly A of said target nucleic acid analyte binds to said oligonucleotide stem region to form a triple helix.

12. A method for detecting a target mRNA analyte in a biological sample, said mRNA having a 3'-poly A region, comprising the steps of:

(a) contacting the sample under hybridization conditions with a capture probe immobilized on a solid surface thereby forming a mRNA:capture probe hybrid, and with a multiplicity of reporter probes, said reporter probes comprising a signal region linked to a homopolymeric sequence comprising $(dT)_n$, $(U)_n$ or $(U')_n$, where n is an integer between 8 and 30, wherein said signal region is comprised of fluorescently-labeled linear or hairpin oligonucleotides; and (b) detecting the fluorescence emitted by the reporter probes hybridized to the 3' poly A region of the mRNA:capture probe hybrid.

13. The method of claim 4, wherein step (a) is performed in solution and step (b) is carried out with an immobilized capture probe.

14. The method of claim 4, wherein steps (a) and (b) are performed in solution, and said analyte:capture probe hybrid formed in step (b) is subsequently bound to a surface for detection thereupon.

15. The method of claim 4, wherein said reporter probes hybridize with said analyte poly A region to form a double helix.

16. The method of claim 4, wherein said reporter probes hybridize with said analyte poly A region to form a triple helix.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: YES ( i v ) ANTI-SENSE: NO ( x i ) SEQUENCE DESCRIPTION: SEQ ID NO:1:

```
A A A A A A A A A A  A A A A A A A A A A  A A A A                                    2 4
```

( 2 ) INFORMATION FOR SEQ ID NO:2:

( i ) SEQUENCE CHARACTERISTICS:
        ( A ) LENGTH: 105 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:2:

```
G G G A C A C T C C  A C C A T A G A T C  A C T C C C C T G T  T T T T C G C A G A  A A G C G T C T A G  C C A T G A A A A A    6 0

A A A A A A A A A A  A A A A A A A A A A  A A A A A A A A A A  A A A A A A A A A A  A A A A A                            1 0 5
```

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( i i i ) HYPOTHETICAL: NO ( i v ) ANTI-SENSE: NO ( x i ) SEQUENCE DESCRIPTION: SEQ ID NO:3:

```
A C A G G G G A G T  G A T C T A T G G T  G G A G T                                   2 5
```

( 2 ) INFORMATION FOR SEQ ID NO:4:

( i ) SEQUENCE CHARACTERISTICS:
        ( A ) LENGTH: 21 base pairs

-continued (B) TYPE: nucleic acid
        (C) STRANDEDNESS: single
        (D) TOPOLOGY: linear (ii) MOLECULE TYPE: other nucleic acid
        (A) DESCRIPTION: /desc = "OLIGONUCLEOTIDE"

(iii) HYPOTHETICAL: NO (iv) ANTI-SENSE: NO (xi) SEQUENCE DESCRIPTION: SEQ ID NO:4:

CATGGCTAGA CGCTTTCTGC G                                                                 2 1

(2) INFORMATION FOR SEQ ID NO:5:

(i) SEQUENCE CHARACTERISTICS:
        (A) LENGTH: 79 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "SYNTHETIC OLIGONUCLEOTIDE"

(iii) HYPOTHETICAL: NO (iv) ANTI-SENSE: NO (ix) FEATURE:
        (A) NAME/KEY: stem_loop
        (B) LOCATION: 1..54

(xi) SEQUENCE DESCRIPTION: SEQ ID NO:5:

CTTCAGCGAC AACTTCGTCA ACGTCGAAAG ACGTTGACGA AGTTGTCGCT GAAGTTTTCA        6 0

TGGCTAGACG CTTTCTGCG                                                    7 9